United States Patent [19]

Finke et al.

[11] 3,972,923
[45] Aug. 3, 1976

[54] PROCESS FOR THE PREPARATION OF PHOSPHONIC ACID DIHALIDES

[75] Inventors: Manfred Finke, Fischbach, Taunus; Hans-Jerg Kleiner, Bad Soden, Taunus; Gerhard Stähler, Frankfurt am Main; Klaus Dehmer, Kelkheim, Taunus, all of Germany

[73] Assignee: Hoechst Aktiengesellschaft, Frankfurt am Main, Germany

[22] Filed: Nov. 13, 1973

[21] Appl. No.: 415,341

Related U.S. Application Data

[63] Continuation-in-part of Ser. No. 262,203, June 13, 1972, abandoned, and Ser. No. 262,204, June 13, 1972, abandoned, and Ser. No. 262,205, June 13, 1972, abandoned.

[30] Foreign Application Priority Data

| | | |
|---|---|---|
| Apr. 6, 1972 | Germany | 2216565 |
| Mar. 29, 1972 | Germany | 2215314 |
| June 15, 1971 | Germany | 2129584 |
| July 2, 1971 | Germany | 2132962 |

[52] U.S. Cl. ................ 260/543 P; 260/465.1; 260/488 F
[51] Int. Cl.² .................................. C07F 9/42
[58] Field of Search ...................... 260/543 P

[56] References Cited
FOREIGN PATENTS OR APPLICATIONS
784,923   12/1972   Belgium .................. 260/543 P

*Primary Examiner*—Lorraine A. Weinberger
*Attorney, Agent, or Firm*—Curtis, Morris & Safford

[57] ABSTRACT

Process for preparing phosphonic acid dihalides of the formula

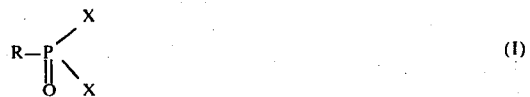

wherein R is alkyl of 1 to 18 carbon atoms, cycloalkyl of 4 to 8 carbon atoms, alkenyl of 2 to 18 carbon atoms, phenyl, phenalkyl or alkyl-phenyl of 7 to 8 carbon atoms, phenyl, phenalkyl or alkyl-phenyl of 7 to 8 carbon atoms, all radicals R optionally being substituted by chlorine, bromine, cyano or lower acyloxy, and wherein X is halogen such as 2-chloroethane phosphonic acid dichloride, by reacting phosphonic or thio-phosphonic acids of the formula

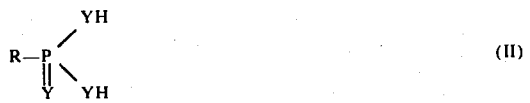

wherein Y is oxygen or sulfur, their salts or functional derivatives, with acid halides of the formula
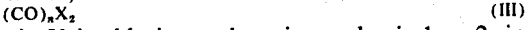
wherein X is chlorine or bromine and $n$ is 1 or 2, in the presence of 0.2 – 5% or in the presence of 0.01 to 0.2% by weight of 1. compounds containing at least one tri- to pentavalent nitrogen or phosphorus atom, which in the case of nitrogen is bound with 1 to 4, in the case of phosphorus with at least 3 valences to organic radicals having up to 20 carbon atoms, two of these valences optionally forming a double bond, or
2. mono-di- or tribasic organic or inorganic fully amidated acids or tri- or pentavalent phosphorus, the N atom of which optionally being substituted by aliphatic radicals having up to 20 carbon atoms, and the organic radicals of which contain up to 20 carbon atoms, if required, in the presence of an inert solvent.

3 Claims, No Drawings

PROCESS FOR THE PREPARATION OF PHOSPHONIC ACID DIHALIDES

This application is a continuation-in-part of Ser. Nos. 262,203, 262,204 and 262,205, now abandoned, all filed June 13, 1972.

The present invention relates to a process for the preparation of phosphonic dihalides.

It is known to react phosphonic acid dialkyl ester with acid chlorides such as $PCl_5$, $SOCl_2$, and $(COCl)_2$ to obtain the corresponding ester chlorides (Houben-Weyl, "Methoden der organischen Chemie", vol. 12/1 (1963), page 415).

Phosphonic acid dichlorides are obtained with $PCl_5$, $PCl_3 + Cl_2$ only at temperatures of more than 100°C (ibid., page 388). However, in this process considerable difficulties are encountered in the separation of the reaction product from the $POCl_3$ formed as by-product.

It has also been proposed to react phosphonic acid dialkyl ester with gaseous thionyl chloride at temperatures of from 130° to 150°C to give the dichlorides (U.S. Pat. No. 2,847,469). Owing to the corrosive effect of the $SOCl_2$ and/or its secondary product $SO_2$, this process places a severe strain on the materials used in the apparatus.

The reaction of methanephosphonic acid di-isopropyl ester with phosgene at a temperature of from 100° to 200°C and a pressure of 25 atmospheres gage has been described in U.S. Pat. No. 3,179,696, however, the yield is only 48.5%. As is stated in the disclosure of that patent, the reaction cannot be performed at a temperature of less than 100°C.

The present invention provides a process for the preparation of phosphonic acid dihalides of the formula

wherein R is alkyl having 1 to 18 carbon atoms, cycloalkyl having 4 to 8 carbon atoms, alkenyl having 2 to 18 carbon atoms, phenyl, phenalkyl or alkyl phenyl both containing a total of 7 to 8 carbon atoms, R may be substituted by chlorine, bromine, a cyano or a lower acyloxy group, and wherein X is halogen, which comprises reacting (thio) phosphonic acids of the formula

wherein Y is oxygen or sulfur, their salts or functional derivatives with acid halides of the formula $(CO)_nX_2$          (III)

wherein X is chlorine or bromine and n is 1 or 2, in the presence of from 0.2 to 5% by weight of 1. compounds containing at least one tri- to pentavalent nitrogen or phosphorus atom, which in the case of nitrogen is bound with 1 to 4, in the case of phosphorus with at least 3 valences to organic radicals having up to 20 carbon atoms, two of these valences optionally forming a double bond, or
2. mono-, di-or tribasic organic or inorganic fully amidated acids of tri- or pentavalent phosphorus, the N atoms of which optionally are substituted by aliphatic radicals having up to 20 carbon atoms, and the organic radicals of which contain up to 20 carbon atoms, if required, in the presence of an inert solvent.

It has also been found that the phosphonic acid dihalides can be prepared, according to the above process with an amount of catalyst in the range of from 0.01 to 0.2% by weight, calculated on the starting product. It has also been found that 2-chloro-ethanephosphonic acid dichloride can be prepared by the above process with the same reduced amount of catalyst.

Besides the saving of catalyst, this reduction of the catalyst amount has in many cases the advantage that - in particular with large-scale mixtures - the reaction mixtures maintain a fluid consistency and are able to be pumped, whereas in the case of higher concentrations there may be viscous reaction phases at times. Besides, the nondistillable residues are also somewhat reduced with a decreasing catalyst concentration. It goes without saying that the optimum concentration varies according to the kind of catalyst and its molar weight.

Functional derivatives of the phosphonic acids of formula II are, for example, phosphonic acid esters of formula IV

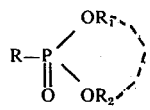

wherein $R_1$ and $R_2$ are alkyl or haloalkyl groups having 1 to 12 carbon atoms, or cycloalkyl groups having 4 to 8 carbon atoms, or together form a straight-chain or branched alkylene group having 2 to 7 carbon atoms; corresponding pyrophosphonic acids, pyrophosphonic acid esters, phosphonic acid monoesters and the salts thereof, phosphonic acid ester halides and phosphonic acid anhydrides as well as the thio-analogs of the above types of compounds, i.e. compounds in which Y is S.

Salts of the (thio) phosphonic acids and (thio) phosphonic acid monoesters are, above all, the alkali salts, in particular the sodium and potassium salts, and the ammonium salts.

Preferred radicals R are alkyl groups having 1 to 12, in particular 1 to 4 carbon atoms, cycloalkyl groups having 4 to 6 carbon atoms, alkenyl groups having 2 to 4 carbon atoms, phenyl, benzyl, chloromethyl, α-chlorethyl, β-chlorethyl, β-chlorpropyl, β-cyanethyl, β-cyanpropyl, β-acetoxyethyl.

$R_1$ and $R_2$ are preferably alkyl groups having 1 to 4 carbon atoms, as well as β-chlorethyl and β-chlorpropyl. Of the phosphonic acid diesters, preference is given to those in which $R_1$ and $R_2$ are identical.

Thus the following compounds, for example, are suitable as starting products:

Methanephosphonic acid, -monomethyl ester, -monoethyl ester, -monoctyl ester, -dimethyl ester, -diethyl ester, -dipropyl ester, -dibutyl ester, -diisobutyl ester, -dihexyl ester, -didodecyl ester, -di-β-chlorethyl ester, -di-β-chloropropyl ester, ethanephosphonic acid, the corresponding ethanephosphonic acid-mono- and diesters, and the like.

As inert solvents there may be used trichloroethane, tetrachloroethane, trichloroethylene, perchloroethylene, toluene, chlorobenzene, dichlorobenzene, diphenylmethane, chloronaphthalene, or even the final product. A preferred solvent is the final product.

As acid halides of formula III, there may be used phosgene, oxalyl-chloride, bromophosgene, and oxalyl-bromide, however, preference is given to phosgene.

The above-mentioned catalytically active nitrogen and phosphorus compounds have the following general formulae:

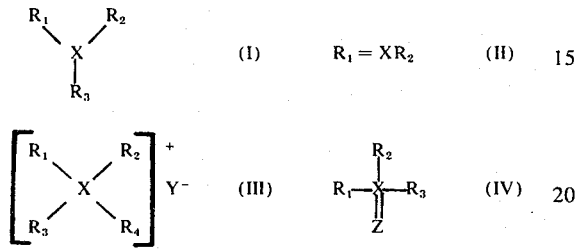

The above ligands have the following meaning:
X is N or P;
Y is an inorganic or organic acid radical;
$R_1$ is an organic radical having from 1 to 20 carbon atoms;
$R_2$ and $R_3$ each are organic radicals having 1 to 20 carbon atoms, or H, if X is N.

In case X is N, one of the ligands $R_1$, $R_2$ or $R_3$ may be the radical of a mono- or polycarboxylic acid, or the radical of an inorganic or organic acid of trivalent or pentavalent phosphorus or of their amides or alkylanides.

$R_4$ is an organic radical having from 1 to 20 carbon atoms, or H, if X is N and at the same time $R_2$ and $R_3$ each are organic radicals; Z is oxygen, or - if X is P - sulfur, 2 halogen atoms, preferably chlorine atoms, or the group $NR_5$, $R_5$ being hydrogen or an organic radical having 1 to 20 carbon atoms.

Inorganic or organic acid radicals are, for example, halogen ions, $SO_4^{--}$, $CH_3OSO_3^-$ or $C_6H_5OSO_3^-$.

$R_1$, $R_2$, $R_3$ and $R_4$ may be identical or different organic radicals, for example straight or branched alkyl groups having 1 to 20, preferably 1 to 12, in particular 1 to 4 carbon atoms, alkenyl groups having 2 to 20, preferably 2 to 12, in particular 2 to 4 carbon atoms, cycloalkyl or cycloalkenyl groups having 4 to 8, preferably 4 to 6 carbon atoms, aryl or aralkyl groups having 6 to 20, preferably 6 to 12 carbon atoms, or acyl groups having 1 to 4, preferably 1 or 2 carbon atoms.

All the radicals R may also be substituted, preferably monosubstituted, by halogen, preferably chlorine or bromine, alcoxy radicals having 1 to 4, preferably 1 to 2 carbon atoms, or a dialkylamino group with alkyl groups having 1 to 4 carbon atoms each.

2 Or 3 of the radicals $R_1$ to $R_4$ may also form a saturated or unsaturated heterocyclic ring, which may contain further hetero-atoms, for example nitrogen, oxygen or sulfur.

If X is N, $R_2$ and/or $R_3$ and, if $R_2$ and $R_3$ are organic radicals, also $R_4$ may be hydrogen.

Finally, it is also possible to use the amides of the different organic or inorganic mono-di-or tribasic acids of trivalent or pentavalent phosphorus as catalysts. These catalysts are peramidated, they contain at the nitrogen atom(s) 2 aliphatic radicals each having up to 20 carbon atoms, preferably alkyl groups having from 1 to 4 carbon atoms, and they carry as organic radical at the phosphorus atom an aliphatic group having up to 20 carbon atoms, preferably an alkyl group having 1 to 4 carbon atoms a cycloalkyl group having 4 to 8 carbon atoms, or a phenyl or benzyl group. The organic radical may also be substituted, preferably by lower alkyl or alcoxy groups or halogen atoms.

The molecular weight of the catalyst used is preferably up to 500, in particular up to 200.

Thus, the following compounds may be used at catalysts:

A. Aliphatic and aromatic amines and phosphines, such as n-butylamine, diethylamine, trimethylamine, tripropylamine, tributylamine, dimethyl-dodecylamine, triphenylamine, trimethylphosphine, triethylphosphine, tripropylphosphine, tributylphosphine, triphenylphosphine, and tris-(p-dimethylaminophenyl)-phosphine and the correspondingly mixed amines, phosphines, phospholanes and phospholenes, such as dimethyl-ethylamine, diethyl-butylamine, N-dimethylaniline, 4-methyl-N-dimethylaniline, N-diethylaniline, N,N'-tetramethyl-p-phenylene diamine, N-ethyl-piperidine, or N-methyl-pyrrolidine; methyl-diethyl-phosphine, dimethylpropylphosphine, diethyl-benzyl-phosphine, 1-methylphospholene-3, and 1-ethyl-3-methyl-phospholene-3;

B. Azomethines, such as hydrobenzamide, benzylidene aniline, o-, m-, p-methyl-, o-, m-, p-methoxy, o-, m-, p-chlorobenzylidene aniline, as well as corresponding derivatives of substituted anilines, for example of o-, m-, or p-toluidine, of o-, m- or p-nitraniline, of o- and p-anisidine or of o-, m- and p-chloroaniline;

C. Quaternary ammonium salts or phosphonium salts such as tetramethylammonium chloride or -bromide, tetraethylphosphonium chloride, trimethyl-benzylammonium chloride, triethylbenzylammonium chloride, triethylbenzylammonium bromide, trimethylbenzylphosphonium chloride, triphenylethylphosphonium-2,4-diamino-benzene-sulfonate, trimethyl-chloromethyl-ammonium chloride;

D. Heterocyclic compounds having an aromatic character, such as pyridine, quinoline, isoquinoline and their alkyl and dialkyl, preferably methyl or dimethyl derivatives, imidazole, N-vinyl-imidazole, benzthiazole, 2-amino-6-ethoxy-benzthiazole, triazole; also phosphabenzenes;

E. Acid amides, such as dimethyl formamide, diethyl formamide, N-dimethyl-acetamide, N-diethyl-propionamide, N-dimethyl-benzamide, N-methyl-pyrrolidone, N,N'-tetramethylterephthalic acid- diamide, or ureas, such as tetramethyl urea and trimethyl-phenyl-urea;

F. Other nitrogen or phosphorus compounds having a higher valency of a N or P atom than 3, such as pyridine-N-oxide, trimethyl-phosphinic oxide, tributyl-phosphonic oxide, trihexyl-phosphinic oxide, triphenyl-phosphinic oxide, dimethyl-phenyl-phosphinic oxide, dimethyl-phenyl-phosphinic sulfide, dimethyl-chloromethyl-phosphinic oxide, dimethyl-cicosylphosphinic oxide, dimethyl-dodecyl-phosphinic oxide, dimethyl-phosphinic oxide, dimethyl-(pyrrolidinyl-1-methyl)-phosphinic oxide, triphenyl-phosphinic-dichloride, dimethyl-dodecyl-phosphinic sulfide, triphenylphosphinimine, dimethyl-chloromethyl-phosphinic-dichloride, N-2-dimethyl-phosphinylethyl-N-methyl-acetamide, N-2-dimethyl-phosphinyl-propionic acid-methyl ester, N-2-dimethyl-phosphinyl-ethyl-methylamine, phospholene oxides, such as 1-methyl-phospholene-1-oxide and 1-ethyl-3-methylphospholene-1-oxide;

G. Amides of phosphinous, phosphonous, phosphinic and phosphonic acids, as well as of their thio-analogs, such as ethanephosphonic acid-bis-diethylamide, methanebutanephosphinous acid-dimethylamide, diethylphosphinous acid-isobutylamide; also triamides of phosphoric and thiophosphoric acid such as hexamethylphosphoric acid-triamide.

All catalysts are used in amounts of 0.2 to 5% by weight, calculated on the phosphonic acid derivative used or preferably in the presence of 0.01 to 0.2% by weight. It is also possible to use larger amounts of catalyst, but besides the increased concumption of material this has the drawback that the reaction mixtures may become too viscous. It goes without saying that the optimum concentration varies with the kind of catalyst and its molar weight. The catalysts may be used as such or in the form of their salts, in particular the hydrochlorides.

The process is carried out preferably at a temperature of from +65°C to 200°C. Higher temperatures are also possible, but offer no advantage. The most preferred reaction temperature is in the range of from +80°C to +150°C.

The reaction may be carried out under pressure, for example at 5 to 10 atmospheres gage or, if there is no intermediate pressure release, also with the higher pressures arising from the formation of $CO_2(CO)$. Nevertheless working under atmospheric pressure is preferred.

The reaction time may vary depending on the temperature and apparatus used for the process. Generally it is in the range of from about 2 to about 7 hours.

An amount of acid halide exceeding the stoichiometrical amount is actually not required, however, it may be advantageous to add an excess amount in order to reduce the reaction time. In such case, the excess acid halide leaving the reaction zone with the exhaust gases is advantageously used up by fresh starting material, suitably in a counter-current column. It is also possible to perform the whole process continuously in known manner, in particular in a column or an equivalent device.

The reaction is suitably carried out by introducing the acid halide into the mixture of phosphonic acid derivative and catalyst and eliminating the by-products (alkyl halide $CO_2$, CO) in known manner - if possible already during the reaction - from the reaction zone, for example by distillation and/or fractional condensation. In some cases it is advantageous to add the catalyst portionwise or in a later phase of the reaction, when it is gradually coming to an end, for example after the formation of the ester halide from ester.

A vigorous mixing is advantageous, particularly if gaseous acid halides such as phosgene are used. After completion of the reaction the reaction product is isolated by way of distillation.

The phosphonic acid halides which may be prepared in accordance with the process of the invention are valuable intermediate products, for example for the preparation of plant protective agents, ripening accelerators and flameproofing agents. 2-chloroethane-phosphonic acid-dichloride is a valuable intermediate product for the preparation of 2-chloroethane-phosphonic acid and its derivatives which are used, for example, as growth regulating agents and ripening accelerators, as well as for the preparation of vinyl phosphonic acid which is used, in a polymerized form, for corrosion protection.

Because of its simplicity the process has essential technical advantages, in particular due to the fact that the by-products are gases or can be distilled off and may thus easily be separated from the reaction products.

The catalyst used for the reaction generally remains during the distillation of the phosphonic acid halides in the residue and can be used again for further reactions.

The process of the invention is particularly suitable for the preparation of 2-chloroethane-phosphonic acid-dichloride from impure 2-chloroethane-phosphonic acid-bis-(2-chloroethyl)-ester, as it is obtained in the process according to Kabachnik et al. (C. A. 42 (1948), 7241-3). According to this process, phosphorus trichloride is first reacted with ethylene oxide to give tris-2-chloroethyl-phosphite, which is subsequently rearranged under heat to form 2-chloroethane-phosphonic acid-bis-(2-chloroethyl)ester. In the course of this process a residue is formed which cannot be distilled off and which when heating with $PCl_5$, in the sealed tube, gives 2-chloroethane-phosphonic acid-dichloride in a moderate yield. The 2-chloroethane-phosphonic acid-bis-(2-chloroethyl)-ester shows a similar reaction. Kabachnik et al. therefore came to the conclusion that the residue was a polycondensation product which supposedly reacted with phosphorus pentachloride according to the following scheme:

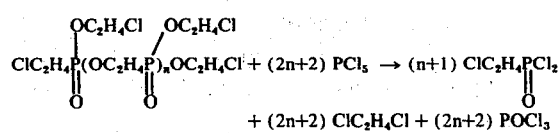

From the raw rearrangement product, Kabachnik and his co-workers obtained 52% of the theory of 2-chloroethane-phosphonic acid-dichloride, according to the above-mentioned method.

In contradistinction thereto, the process of the invention gives 2-chloroethane-phosphonic acid-dichloride in a yield which (depending on the catalyst) is as a rule more than 70%, in many cases even more than 80%.

The reaction processes may be represented by the following scheme:

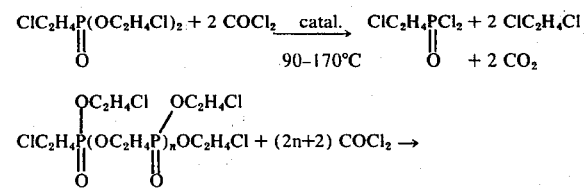

("polycondensation product")

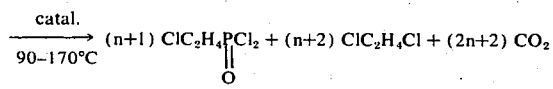
$$\xrightarrow[90-170°C]{catal.} (n+1) \text{ClC}_2\text{H}_4\overset{\underset{\parallel}{O}}{\text{P}}\text{Cl}_2 + (n+2) \text{ClC}_2\text{H}_4\text{Cl} + (2n+2) \text{CO}_2$$

Besides 2-chloroethane-phosphonic acid-dichloride, vinyl-phosphonic acid-dichloride is obtained in varying amounts of from 5 to 20% of the total reaction product depending on the physical conditions of the reaction, the catalyst and its amount. It can easily be separated from the main product by way of distillation. As a rule, the proportion of vinyl-phosphonic acid-dichloride is reduced with decreasing catalyst concentration and decreasing temperature, in favour of the formation of 2-chloroethane-phosphonic acid-dichloride.

The decomposition of the raw 2-chloroethane-phosphonic acid-bis-2-chloroethyl ester with phosgene in order to prepare 2-chloroethane-phosphonic acid-dichloride has the advantage, as compared with the above-mentioned prior art, that no special apparatuses are required. The process may be carried out under normal pressure.

Surprisingly, the non-distillable residue obtained by the addition of ethylene oxide to phosphorus trichloride (cf. scheme II) to form tris-2-chloroethyl-phosphite can also be decomposed to give 2-chloroethane-phosphonic acid-dichloride in the same way as was effected with 2-chloroethane-phosphonic acid-bis-2-chloroethyl ester.

It is therefore possible to carry out the reaction of phosphorus trichloride with ethylene oxide, the subsequent rearrangement of the tris-(2chloroethyl)-phosphite thus formed to give 2-chloroethane-phosphonic acid-bis-(2-chloroethyl ester), and the further reaction of the reaction products having been formed in this process with phosgene to yield 2-chloroethane-phosphonic acid-dichloride, in a single reaction vessel and without intermediate purification, with good results.

The following Examples serve to illustrate the invention.

EXAMPLE 1

Preparation of ethane-phosphonic acid-dichloride from ethane-phosphonic acid-dimethylester with phosgene 126 g of ethane-phosphonic acid-dimethylester and 0.5 g of triphenyl-phosphine were introduced into a cylindrical vessel having a diameter of 4 cm and a length of 25 cm. At a temperature of from 100° to 110°C, phosgene was slowly introduced, while stirring rapidly, through a frit sealed in the bottom of the vessel. After 6 hours the phosgene current was stopped, and the excess phosgene was blown off with nitrogen at room temperature. The reaction product was distilled under reduced pressure, and 125 g of gaschromatographically pure ethanephosphonic acid-dichloride (boiling point of 71°C under a pressure of 15 mm of mercury) were obtained. This corresponded to a yield of 96% of the theory.

EXAMPLE 2

Preparation of ethane-phosphonic acid-dichloride from ethane-pyrophosphonic acid-dimethylester As in Example (1) phosgene was introduced for 6 hours at a temperature of from 100° to 120°C into 56 g of ethanepyrophosphonic acid-dimethylester in the presence of 0.5 g of triphenyl-phosphine. Excess phosgene was eliminated with nitrogen at room temperature and the reaction solution was subsequently distilled under reduced pressure. At a boiling point of 58°C under a pressure of 9 mm of mercury, 67 g of ethane-phosphonic acid-dichloride were distilled. This corresponded to a yield of 94% of the theory.

EXAMPLE 3

Preparation of ethane-phosphonic acid-dichloride from ethane-phosphonic acid-anhydride In a manner analogous to Example (1), phosgene was introduced for 4 hours, at a temperature of from 100° to 120°C, into a solution of 71 g of ethane-phosphonic acid-anhydride and 0.7 g of pyridine in 71 g of ethane-phosphonic acid-dichloride. After the blowing-off of the excess phosgene with nitrogen and subsequent distillation of the reaction solution under reduced pressure 183 g of ethane-phosphonic acid dichloride were obtained having a boiling point of 58°C under a pressure of 9 mm of mercury. The yield was thus (183 g – 71 g =) 112 g of ethane-phosphonic acid-dichloride = 99% of the theory.

EXAMPLES 4 to 46

Further experiments analogous to Example 1, which were carried out while using different phosphonic acid derivatives and different catalysts, are summarized in the following Table.

Table

| Phosphonic acid derivatives | Catalyst | Temp. (°C) | Reaction time | Yield |
|---|---|---|---|---|
| 4) $\text{CH}_3\text{CH}_2\overset{\underset{\parallel}{O}}{\text{P}}\begin{smallmatrix}\nearrow\text{OC}_2\text{H}_5\\ \searrow\text{OC}_2\text{H}_5\end{smallmatrix}$ | pyridine 0.5 % | 100–120 | 6 hours | 93 % |
| 5) $\text{CH}_3\text{CH}_2\overset{\underset{\parallel}{O}}{\text{P}}\begin{smallmatrix}\nearrow\text{OC}_2\text{H}_5\\ \searrow\text{OC}_2\text{H}_5\end{smallmatrix}$ | dimethyl-formamide 1 % | 95–100 | 5.5 hours | 75 % |
| $\text{C}_2\text{H}_5\overset{\underset{\parallel}{O}}{\text{P}}\begin{smallmatrix}\nearrow\text{OC}_2\text{H}_5\\ \searrow\text{OC}_2\text{H}_5\end{smallmatrix}$ | hexamethyl-phosphoric acid triamide 5 % | 95–100 | 5 hours | 88 % |

Table-continued

| Phosphonic acid derivatives | Catalyst | Temp. (°C) | Reaction time | Yield |
|---|---|---|---|---|
| 6) $C_2H_5\text{-P(=O)(OC}_2H_5)_2$ | triethyl-benzyl-ammonium-chloride 1 % | 100–110 | 5 hours | 97.5 % |
| 7) $C_2H_5\text{-P(=O)(OC}_2H_5)_2$ | N-2-dimethyl-phosphinyl-ethyl-methyl-acetamide 1 % | 100 | 5.5 hours | 92.5 % |
| 8) $C_2H_5\text{-P(=O)(OC}_2H_5)_2$ | ethane-phosphonic acid-N',N'-bis-di-ethylamide 1.5 % | 100 | 5 hours | 85 % |
| 9) $C_2H_5\text{-P(=O)(OC}_2H_5)_2$ | trimethyl-phosphinic oxide 1 % | 110 | 5.75 hours | 77 % |
| 10) $C_2H_5\text{-P(=O)(OC}_2H_5)_2$ | triphenyl-phosphine 1 % | 90–100 | 5 hours | 89 % |
| 11) $C_2H_5\text{-P(=O)(OC}_2H_5)(Cl)$ | 2-amino-6-ethoxy-benzthiazole 1 % | 130 | 6 hours | 87 % |
| 12) $(CH_3)_2CHCH_2\text{-P(=O)(OCH}_3)_2$ | pyridine 1 % | 90 | 5.5 hours | 82 % |
| 13) $C_8H_{17}\text{-P(=O)(OC}_2H_5)_2$ | pyridine 1 % | 130 | 7 hours | 90 % |
| 14) $C_{12}H_{25}\text{-P(=O)(OC}_2H_5)_2$ | pyridine 1 % | 130 | 6.5 hours | 90 % |
| 15) $C_6H_5\text{-P(=O)(OC}_2H_5)_2$ | triphenyl-phosphine 1 % | 100–110 | 7 hours | 92 % |
| 16) $C_2H_5\text{-P(=O)(OCH}_2CH(CH_3)_2)_2$ | pyridine 1% | 130–140 | 5 hours | 90 % |
| 17) $C_6H_5CH_2\text{-P(=O)(OC}_2H_5)_2$ | pyridine 1 % | 100–120 | 6 hours | 94 % |
| 18) $C_6H_5CH_2\text{-P(=O)(OC}_2H_5)_2$ | tributyl-phosphine 1 % | 100–120 | 6 hours | 90 % |
| 19) $CH_2=CH\text{-P(=O)(OC}_2H_5)_2$ | triphenyl-phosphine 1 % | 100–120 | 6 hours | 91.5 % |
| 20) $ClCH_2CH_2\text{-P(=O)(OC}_2H_5)_2$ | triphenyl-phosphine 1 % | 80–100 | 6 hours | 89 % |
| 21) $ClCH_2CH_2\text{-P(=O)(OCH}_3)_2$ | dimethyl-formamide 1 % | 95 | 6 hours | 81 % |

Table-continued

| Phosphonic acid derivatives | Catalyst | Temp. (°C) | Reaction time | Yield |
|---|---|---|---|---|
| 22) $C_2H_5\overset{\overset{O}{\|}}{P}(OC_2H_5)(Cl)$ | triphenyl-phosphine 1 % | 105–110 | 5 hours | 95 % |
| 23) $CH_3\overset{\overset{O}{\|}}{P}(Cl)(OCH(CH_3)_2)$ | pyridine 1 % | 115–120 | 7 hours | 72 % |
| 24) $CH_3COOCH_2CH_2\overset{\overset{O}{\|}}{P}(OC_2H_5)_2$ | dimethyl-formamide 1 % | 95–100 | 7 hours | 83 % |
| 25) $CH_3CH_2\overset{\overset{O}{\|}}{P}(OC_2H_5)_2$ | $[(CH_3)_2CH]_2NP(C_2H_5)_2$ 1 % | 100–110 | 5 hours | 90 % |
| 26) $C_2H_5\overset{\overset{O}{\|}}{P}(OC_2H_5)_2$ | 2-dimethyl-phosphinyl-ethyl-methyl-amine 1 % | 100–120 | 5–6 hours | 90 % |
| 27) $C_2H_5\overset{\overset{O}{\|}}{P}(OC_2H_5)(Cl)$ | pyridine-N-oxide 1 % | 100–120 | 6 hours | 90 % |
| 28) $C_2H_5\overset{\overset{O}{\|}}{P}(OC_2H_5)_2$ | acetic acid methyl-2-dimethyl-phosphinyl-ethylamide 1 % | 100 | 5.5 hours | 93 % |
| 29) $C_2H_5\overset{\overset{O}{\|}}{P}(OCH_3)_2$ | triphenyl-phosphinic oxide 1 % | 110 | 5 hours | 93 % |
| 30) $CH_3CH_2CH_2\overset{\overset{O}{\|}}{P}(OCH_3)_2$ | dimethyl-phenyl-phosphinic oxide 1 % | 110 | 5 hours | 91 % |
| 31) $CH_3CH_2CH_2\overset{\overset{O}{\|}}{P}(OC_2H_5)_2$ | dimethyl-phenyl-phosphinic sulfide 1 % | 85–105 | 6 hours | 87 % |
| 32) $CH_3CH_2CH_2\overset{\overset{O}{\|}}{P}(OC_2H_5)_2$ | dimethyl-chloromethyl-phosphinic oxide 1.5 % | 105 | 6 hours | 90 % |
| 33) $C_6H_5\overset{\overset{O}{\|}}{P}(OC_2H_5)_2$ | dimethyl-hexyl-phosphinic oxide 1.5 % | 120 | 4.5 hours | 90 % |
| 34) $ClCH_2CH_2\overset{\overset{O}{\|}}{P}(OCH_3)_2$ | dimethyl-dodecyl-phosphinic oxide 1 % | 85–100 | 6 hours | 89 % |
| 35) $C_8H_{17}\overset{\overset{O}{\|}}{P}(OC_2H_5)_2$ | dimethyl-eicosyl-phosphinic oxide 1.5 % | 130 | 5 hours | 87 % |
| 36) $C_6H_{13}\overset{\overset{O}{\|}}{P}(OCH_3)_2$ | 2-dimethyl-phosphinyl-propionic acid-methyl-ester 1 % | 130 | 4.5 hours | 85 % |
| 37) | | | | |

Table-continued

| Phosphonic acid derivatives | Catalyst | Temp. (°C) | Reaction time | Yield |
|---|---|---|---|---|
| 38) $CH_3CH_2\overset{O}{\underset{\parallel}{P}}\!\!\begin{array}{l}OC_2H_5\\OC_2H_5\end{array}$ | 1-methyl-phospholene-(3)-oxide 1 % | 120 | 5 hours | 93 % |
| 39) $CH_3COOCH_2CH_2\overset{O}{\underset{\parallel}{P}}\!\!\begin{array}{l}OC_2H_5\\OC_2H_5\end{array}$ | quinoline 0.8 % | 120 | 5 hours | 90 % |
| 40) $C_6H_5CH_2\overset{O}{\underset{\parallel}{P}}\!\!\begin{array}{l}OC_2H_5\\OC_2H_5\end{array}$ | pyrrolidinyl methyl-di-methyl-phosphinic oxide 1 % | 110 | 4.5 hours | 95 % |
| 41) $CH_3\text{-}C_6H_4\text{-}CH_2\overset{O}{\underset{\parallel}{P}}\!\!\begin{array}{l}OC_2H_5\\OC_2H_5\end{array}$ | 1-vinyl-imidazole 0.9% | 115 | 6 hours | 91 % |
| 42) $CH_3CH_2\overset{O}{\underset{\parallel}{P}}\!\!\begin{array}{l}OC_2H_5\\OC_2H_5\end{array}$ | dimethyl-aniline 1.5 % | 115 | 6 hours | 86 % |
| 43) $CH_3CH_2\overset{O}{\underset{\parallel}{P}}\!\!\begin{array}{l}OCH_3\\OCH_3\end{array}$ | triphenyl-ethyl-phos-phonium-chloride 1 % | 110 | 4.5 hours | 90 % |
| 44) $CH_3\overset{O}{\underset{\parallel}{P}}\!\!\begin{array}{l}OC_2H_5\\OC_2H_5\end{array}$ | tetramethyl-urea 2 % | 120 | 6 hours | 90 % |
| 45) $CH_3CH_2\overset{O}{\underset{\parallel}{P}}\!\!\begin{array}{l}OCH_3\\OCH_3\end{array}$ | p-methoxy-benzylidene-p-n-butyl-aniline 1 % | 130 | 8 hours | 85 % |
| 46) $CH_3CH_2\overset{O}{\underset{\parallel}{P}}\!\!\begin{array}{l}OCH_3\\OCH_3\end{array}$ | triphenyl-phosphonium-sulfate 1 % | 110 | 4 hours | 99 % |

EXAMPLE 47

Preparation of chloroethane-phosphonic acid-dichloride from chloroethane-phosphoric acid-bis-(2-chloroethyl)-ester A cylindrical vessel made of glass and having a diameter of 7 cm and a height of 20 cm provided with a thermometer tube and a frit placed at the bottom and connected with a gas inlet tube, was immersed into a heating bath up to half its height. The vessel was connected with a two-neck flask having a capacity of 500 ccm and serving as receiver, the second nozzle of which being connected with a gas outlet tube, via a glass tube attached vertically at the top and a descending cooler, which was cooled to a temperature of from 20° to 40°C.

600 g (2.2 moles) of 2-chloroethane-phosphonic acid-bis-2-chloroethyl-ester and 3 g of triphenyl-phosphine were introduced into a cylindrical vessel. About 800 g (8 moles) of phosgene were then introduced during about 4 hours in a strong current through the frit at the bottom at a heating bath temperature of from 120° to 130°C. Owing to the reaction heat developing in the course of the process the reaction temperature was maintained at the level of the heating bath temperature or was slightly higher. Towards the end of the reaction the reaction temperature decreased by 10° to 15°C, with the bath temperature remaining constant.

23 g of vinyl-phosphonic acid-dichloride having a boiling point of from 48 to 49°C/6 Torr Hg (7% of the theory) and 375 g of 2-chloroethane-phosphonic acid-dichloride having a boiling point of from 93 to 94°C/6 Torr Hg (89% of the theory) were obtained by way of fractional distillation of the reaction mixture.

The 1,2-dichloroethane obtained from the receiver and the first runnings of the distillation was freed from the dissolved phosgene by washing with a diluted ammonia solution.

420 g of 1,2-dichloroethane were obtained. This corresponded to a yield of 95% of the theory.

EXAMPLE 48

Preparation of chloroethane-phosphonic acid-dichloride from phosphorus trichloride and ethylene oxide in the single-pot process 500 g of ethylene oxide were introduced during 3 to 4 hours at a temperature of from 30° to 40°C while cooling, into a mixture of 500 g of phosphorus trichloride and 200 g of chlorobenzene in a 1 liter cylindrical reaction vessel made of glass and provided with stirrer, reflux condenser, thermometer and a gas inlet tube reaching to the bottom of the vessel, the end of the tube being provided with a frit. After completion of the gas introduction, the reflux condenser was connected by means of a glass transition piece with a two-neck glass flask via a descending cooler.

The reaction mixture obtained which consisted virtually of tris-(2-chloroethyl)-phosphite was then heated at a temperature of from 155° to 160°C in order to effect the rearrangement. The dichloroethane formed in the course of the rearrangement was distilled off from time to time by increasing the temperature of the cooling water in the reflux condenser to 90° – 100°C. In the course of this process 60 g of dichloroethane were obtained.

After a period of 6 to 7 hours the rest of dichloroethane and the chlorobenzene used as solvent were distilled off, after the reflux condenser had been emptied, by applying a vacuum of from 20 to 100 Torr Hg. The remaining residue (906 g) was treated with phosgene at a temperature of from 120° to 140°C, after 9 g of quinoline had been added as catalyst through the above-mentioned gas inlet tube, until after 6 hours no more dichloroethane was formed. After the excess phosgene had been blown off the reaction mixture by means of dry nitrogen, the reaction product was distilled in vacuo.

570 g of a raw distillate having a boiling point of from 40 to 80°C under a pressure of 2 mm of mercury, as well as 40 g of residue were obtained.

According to a gas chromatographic analysis the raw distillate contained 89.8% of 2-chloroethane-phosphonic acid-dichloride and 6.6% of a vinyl-phosphonic acid-dichloride, corresponding to 77.5% of the theory of 2-chloroethane-phosphonic acid-dichloride, and 7.2% of the theory of vinyl-phosphonic acid-dichloride, calculated on the phosphorus trichloride used.

The raw distillate could be separated by way of column-distillation.

EXAMPLE 49

Preparation of chloroethane-phosphonic acid-dichloride from the condensation product 500 g of the distillation residue obtained in the process of the rearrangement of tris-chloroethyl-phosphite to form 2-chloroethane-phosphonic acid-bis-2-chloroethylester were treated with phosgene in a cylindrical glass vessel having a capacity of 500 ml, through a frit sealed in the bottom, after 5 g of pyridine had been added. In the course of this process the reaction temperature rose to 145°C, with a heating bath temperature of 140°C. For condensation of the dichloroethane formed, the waste gases were led through a cooler. After 3 hours the temperature of the reaction mixture dropped to 120°C with the bath temperature remaining constant. 550 g of phosgene were introduced altogether. The reaction mixture was freed from the residual phosgene in the usual manner and was then distilled in vacuo.

Besides 45 g of distillation residue 302 g of a raw distillate were obtained, which contained- according to the analysis effected by gas chromatography - 85% of 2-chloroethane-phosphonic acid-dichloride and 6% of vinyl-phosphonic acid-dichloride. By way of redistillation of the raw distillate over a column 240 g of 2-chloroethane-phosphonic acid-dichloride having a boiling point of from 88 to 89°C/6 Torr Hg and 15 g of vinyl-phosphonic acid-dichloride having a boiling point from 47 to 48°C/6 Torr Hg were obtained.

EXAMPLE 50

In the reaction vessel described in Example 49, 700 g of raw 2-chloroethane-phosphonic acid-bis-2-chloroethylester containing 30% of non-distillable proportion were treated with phosgene at a temperature of from 130° to 135°C in the presence of 5 g of triphenyl-phosphinic oxide as catalyst until after 4 hours no dichloroethane was distilling off any more with the waste gases.

The reaction product was worked up as described in Example 49.

429 g of a raw distillate were obtained, besides 25 g of residue. According to gaschromatographical analysis the raw distillate contained 90% of chloroethane-phosphonic acid-dichloride and 7% of vinyl-phosphinic acid-dichloride.

EXAMPLES 51 to 90

In a manner analogous to Example (1), 2-chloroethane-phosphonic acid-dichloride and vinyl-phosphonic acid-dichloride were prepared from 2-chloroethane-phosphonic acid-bis-2-chloroethylester under the following conditions:

| Catalyst (% by wt.) | reaction temp. (°C) | reaction time (hours) | yield (% of the th.) $ClC_2H_4POCl_2$ | $CH_2=CHPOCl_2$ |
|---|---|---|---|---|
| 51) $(C_6H_5)_3P$ 2 % | 140–150 | 5 | 75 | 14.2 |
| 52) $(C_6H_5)_3P$ 1 % | 140–150 | 3 | 80 | 14 |
| 53) $(C_6H_5)_3P$ 0,25 % | 130–140 | 11 | 89 | 6 |
| 54) $(C_6H_5)_3P=O$ 1 % | 140–145 | 3 | 74 | 20 |
| 55) $(CH_3)_2{>}P=O\ C_6H_5$ 1% | 153–160 | 2.5 | 71 | 20 |
| 56) $(CH_3)_2{>}P=S\ C_6H_5$ 1 % | 140–147 | 2 | 80 | 7.4 |

| Catalyst (% by wt.) | reaction temp. (°C) | reaction time (hours) | yield (% of the th.) ClC₂H₄POCl₂ | CH₂=CHPOCl₂ |
|---|---|---|---|---|
| 57) (CH₃)₂(C₁₂H₂₅)P=O 1% | 150–157 | 1.5 | 68 | 22 |
| 58) (CH₃)₂(C₆H₁₃)P=O 1% | 140–150 | 2 | 69 | 20.5 |
| 59) (CH₃)₂(ClCH₂)P=O 1% | 140–145 | 2 | 78 | 15 |
| 60) (CH₃)₂(C₂₀H₄₁)P=O 2% | 135–140 | 4 | 71.5 | 5.7 |
| 61) (CH₃)₂P(O)C₂H₄—COOCH₃ 1% | 140–150 | 4 | 62 | 12 |
| 62) (phospholene oxide) 1% | 150–155 | 2.5 | 70 | 13.5 |
| 63) (CH₃)₂P(O)—CH₂—N(pyrrolidine) 1% | 135–140 | 3 | 82 | 4.7 |
| 64) pyridine 1% | 140–150 | 2 | 59 | 23 |
| 65) isoquinoline 1% | 130 | 2 | 77.4 | 8.6 |
| 66) CH₂=CH—N(imidazole) 1% | 145–150 | 2 | 78.5 | 15.2 |
| 67) N(C₂H₅)₃ | 140–145 | 2 | 81 | 9.5 |
| 68) (C₂H₅)₃N⁺—CH₂C₆H₅ Cl⁻ 1% | 140–145 | 2 | 76 | 15 |
| 69) (C₆H₅)₃P⁺C₂H₅ ⁻SO₃C₆H₄NH₂ 1% | 140–150 | 2 | 81 | 11 |
| 70) [(CH₃)₂N]₃P=O 1% | 145–150 | 2½ | 74.5 | 11.5 |
| 71) pyridine-N-oxide 1% | 140–155 | 1.25 | 67 | 25 |
| 72) C₆H₅—N(CH₃)₂ 1% | 145–155 | 2 | 74.3 | 14.4 |

-continued
| Catalyst (% by wt.) | reaction temp. (°C) | reaction time (hours) | yield (% of the th.) ClC$_2$H$_4$POCl$_2$ | CH$_2$=CHPOCl$_2$ |
|---|---|---|---|---|
| 73) N(CH$_3$)$_3$ 1 % | 140–150 | 1.5 | 68 | 24 |
| 74) [(CH$_3$)$_2$N]$_2$CO 1 % | 145–155 | 1.5 | 72 | 24 |
| 75) (CH$_3$)$_2$NCHO 1 % | 130–145 | 2 | 78 | 12 |
| 76) (C$_2$H$_5$)$_2$P—N(iso C$_3$H$_7$)$_2$ 0,5 % | 130–150 | 3.5 | 54.5 | 26.5 |
| 77) (n-C$_4$H$_9$)$_3$P 1 % | 110–150 | 5 | 65 | 11 |
| 78) (C$_6$H$_5$)$_3$P=NC$_2$H$_4$OH 1 % | 150–160 | 1.5 | 74 | 16.3 |
| 79) 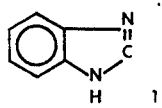 1 % | 140–150 | 2.5 | 64 | 19.8 |
| 80) (C$_2$H$_5$)$_2$NH 1 % | 145–150 | 6 | 60 | 15 |
| 81) 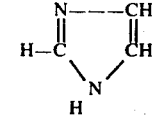 1 % | 150–160 | 2 | 75 | 17 |
| 82) 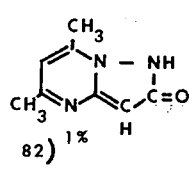 1 % | 150 | 6 | 67 | 15.1 |
| 83) 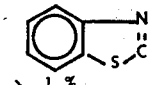 1 % | 150 | 2 | 74 | 21.3 |
| 84) 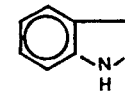 1 % | 160 | 3.5 | 76 | 10.8 |
| 85) (CH$_3$)$_2$PC$_2$H$_4$SO$_2$F ‖ O 1 % | 160 | 1$^h$ 20' | 68 | 10.9 |

| Catalyst (% by wt.) | reaction temp. (°C) | reaction time (hours) | analysis (% of the th.) ClC₂H₄POCl₂ | CH₂=CHPOCl₂ |
|---|---|---|---|---|
| 86) 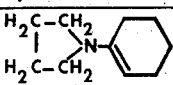 1% | 150 | 1.5 | 78 | 13.2 |
| 87) 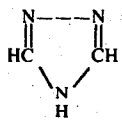 1% | 160 | 2ʰ 20' | 69 | 19.1 |
| 88)  1% | 150 | 2.5 | 73.2 | 16.5 |
| 89) (CH₃)₂NCH₂CN 1% | 147 | 2 | 60 | 4.8 |
| 90) C₄H₉NH₂ 3% | 140–150 | 4 | 53.8 | 6.1 |

EXAMPLE 91

At a temperature of from 130° to 140°C phosgene was introduced for 20 hours into a mixture of 239 g of ethane-phosphonic acid and 4 g of pyridine. After eliminating the phosgene by means of water jet vacuum at 100°C the reaction mixture was distilled. 293 g of ethane-phosphonic acid-dichloride were obtained. This corresponded to a yield of 92% of the theory.

EXAMPLE 92

At a temperature of from 135° to 140°C phosgene was introduced for about 6.5 hours into a mixture of 150 g of octane-phosphonic acid and 1.5 g of triethylamine. After eliminating the phosgene by means of water jet vacuum at 100°C the reaction mixture was distilled. 163.5 g of octane-phosphonic acid-dichloride having a boiling point of 98°C/0.4 Torr Hg were obtained. This corresponded to a yield of 91.5% of the theory.

EXAMPLE 93

43.5 g of benzyl-phosphonic acid and 0.2 g of pyridine were heated at 170°C, and phosgene was introduced for about 5 hours. After eliminating the phosgene by means of water jet vacuum at 100°C the reaction mixture was distilled. 51 g of benzyl-phosphonic acid-dichloride were obtained having a boiling point of 103°C/0.3 Torr Hg, and having a melting point of from 60° to 62°C. This corresponded to a yield of 100% of the theory.

EXAMPLE 94

50 g of octane-phosphonic acid-monosodium salt were suspended in 200 ml of chlorobenzene, then 0.5 g of pyridine were added and were heated at 120°C. At this temperature, phosgene was introduced for 8 hours, while stirring vigorously. Then the reaction mixture was cooled, and the precipitated sodium chloride was filtered off with suction. The filtrate was then freed under a water jet vacuum from the dissolved phosgene and from chlorobenzene. The residue was distilled. 45 g of octane-phosphonic acid-dichloride were obtained. This corresponded to a yield of 84% of the theory.

EXAMPLE 95

14 g of benzene-phosphonic acid and 0.1 g of pyridine were dissolved in 50 ml of chlorobenzene and were heated at 110°C. At this temperature, phosgene was introduced for 6 hours. Subsequently, the reaction solution was blown off with nitrogen, and was then distilled under reduced pressure. 13.5 g of benzene-phosphonic acid dichloride were obtained having a boiling point of 88°C under a pressure of 0.6 mm of mercury. This corresponded to a yield of 78% of the theory.

EXAMPLE 96

Into a mixture of 60 g of chloromethane-phosphonic acid, 16 g of chloromethane-phosphonic acid dichloride and 0.5 g of pyridine, phosgene was introduced for 25 hours at a temperature of from 130° to 140°C, and after addition of 1g of triethylamine, again for 3 hours at 150°C. The reaction solution was blown off with nitrogen and was distilled under reduced pressure. 83 g of chloromethane-phosphonic acid-dichloride were obtained having a boiling point of 82°C under a pressure of 11 mm of mercury. This corresponded to a yield of 86% of the theory.

EXAMPLE 1A: n-butane-phosphonic acid-dichloride

In the presence of 0.1 g of triethylamine and at a temperature of from 110° to 130°C, 900 g of n-butane-phosphonic acid-diethylester were treated with phosgene introduced through a frit at the bottom of a cylindrical vessel having a capacity of 1 liter until the exhaust gases were free of ethyl chloride.

The distillation of the reaction mixture yielded 760 g of n-butane-phosphonic acid-dichloride, b.p. 90° – 92°/14 Torr (94 % of the theory).

EXAMPLE 2A: isobutane-phosphonic acid-dichloride

In the presence of 0.1 g of 1-methyl-phospholene-3 and at a temperature of from 100° to 130°C, 600 g of isobutane-phosphonic acid-diethylester were treated with phosgene in a cylindrical vessel provided with a frit placed at the bottom until the exhaust gases were free of ethyl chloride.

The distillation yielded 495 g of isobutane-phosphonic acid-dichloride having a boiling point of from 86° to 88° /14 Torr (91.5% of the theory).

EXAMPLE 3A: n-propane-phosphonic acid-dichloride

In a manner analogous to Example 2A, 600 g of n-propane-phosphonic acid-diethylester treated with phosgene in the presence of 0.1 g of 1-vinyl-imidazole yielded 490 g of n-propane-phosphonic acid-dichloride, b.p. 80° to 83°/14 Torr (90.5 % of the theory).

EXAMPLE 4A: ethane-phosphonic acid-dichloride

At a temperature of 120°C, phosgene was introduced for 30 hours, while stirring, into 100 g of ethane-phosphonic acid-diethylester, in the presence of 0.01 g of triphenyl-phosphine. For elimination of the excess phosgene, the reaction product was cleansed with nitrogen at room temperature and was distilled under reduced pressure.

70 g of ethane-phosphonic acid-dichloride were obtained having a boiling point of 71° /15 Torr (79 % of the theory).

EXAMPLE 5A: 2-acetoxy-ethane-phosphonic acid-dichloride

At a temperature of 125°C, phosgene was introduced for 9 hours, while stirring, into 200 g of 2-acetoxy-ethane-phosphonic acid-diethylester, after adding 0.1 g of pyridine. For elimination of the excess phosgene, the reaction product was cleansed with nitrogen at room temperature and was distilled under reduced pressure. 164 g of 2-acetoxy-ethane-phosphonic acid-dichloride were obtained having a boiling point of 88° /0.2 Torr (90 % of the theory).

EXAMPLE 6A: ethane-phosphonic acid-dichloride 250 g of ethane-phosphonic acid-dimethylester and 125 mg of triethylamine were introduced into a cylindrical vessel having a diameter of 4 cm. At a temperature of from 100° to 120°C, phosgene was introduced in a strong current, during 12 hours, through a frit sealed in the bottom of the vessel. Subsequently the phosgene dissolved in the reaction mixture was eliminated by applying a water jet vacuum at room temperature. The residue was distilled.

255 g of ethane-phosphonic acid-dichloride were obtained having a boiling point of 71°/15 Torr (96 % of the theory).

Results analogous to those of the Examples given above were obtained using a catalysts dimethyl formamide, hexamethyl-phosphoric acid-triamide, triethyl-benzyl-ammoniumchloride, N-2-dimethyl-phosphinylethyl-methylacetamide, ethane-phosphonic acid-N',N'-bis-diethylamide, trimethyl-phosphinic oxide, 2-amino-6-ethoxy-benzthiazole, tributyl-phosphine, 2-dimethyl-phosphinylethyl-methylamine, pyridine-N-oxide, acetic acid-methyl-2-dimethylphosphinylethylamide, dimethyl-phenyl-phosphinic oxide, dimethyl-phenylphosphinic sulfide, dimethyl-chloromethylphosphinic oxide, dimethyl-hexyl-phosphinic oxide, dimethyl-dodecyl-phosphinic oxide, dimethyl-n-eicosyl-phosphinic oxide, 2-dimethylphosphinyl-propionic acid-methylester, 1-methyl-phospholene-(3)-oxide, quinoline, pyrrolidinyl-N-methyl-dimethylphosphinic oxide, dimethylaniline, triphenyl-ethyl-phosphonium chloride, tetramethylurea, p-methoxy-benzylidene-p-n-butyl-aniline, triphenyl-phosphonium sulfate, dimethyl-phosphinous acid-diisopropylamide, triphenyl-phosphinic oxide.

The following Examples 1B and 2B, which serve to illustrate the further aspects of the invention, were carried out in a gassing device consisting of a vertical glass tube having a diameter of 225 mm and a length of 2000 mm; the capacity was about 80 liters. The device was charged each time with 85 kg (316 moles) of raw 2-chloroethane-phosphonic acid-bis-2-chloroethylester and was heated at 150° C by means of a heating coil. Phosgene was introduced from the bottom (a total of 85 kg = 860 moles, corresponding to 136% of the theory). The reaction time was in each case about 20 hours. In the course of the gassing process the reaction mixture was constantly cycled in the counter-current, i.e., it was drawn off at the lower end of the tube and was transported to the head of the device by means of a pump. In the Examples 1B and 2B about 55 kg of phosphonic acid dichloride were obtained containing up to 10% of vinyl-phosphonic acid-dichloride. The raw product contained also varying amounts of dichloroethane, as well as smaller amounts of HCl and $COCl_2$, which could be largely eliminated by blowing nitrogen through the hot solution. The molar percentages indicated in the Examples 1B and 2B for the catalyst are calculated on the basis of the starting product used.

EXAMPLE 1B

Catalyst: triphenyl-phosphine

| amount g | catalyst weight % | mole % | working-up of the raw product distillate % | residue % |
|---|---|---|---|---|
| 85 | 0.10 | 0.10 | 93 | 5.3 |

EXAMPLE 2B

Catalyst: triethylamine

| amount g | catalyst weight % | mole % | working-up of the raw product distillate % | residue % |
|---|---|---|---|---|
| 115 | 0.14 | 0.35 | 91 | 6.0 |
| 80 | 0.09 | 0.24 | 92 | 5.5 |
| 40 | 0.05 | 0.12 | 92 | 5.0 |

Results analogous to those in Examples 1B and 2B were obtained using as catalysts for example quinoline, pyridine, triphenyl-phosphinic oxide, dimethyl-phenyl-phosphinic sulfide, dimethyl-hexyl-phosphinic oxide, dimethyl-chloromethyl-phosphinic oxide, dimethyl-dodecyl-phosphinic sulfide, dimethyl-phenyl-phosphinic oxide, dimethyl-dodecyl-phosphinic oxide, dimethyl-n-eicosyl-phosphinic oxide, 2-dimethyl-phosphinyl-propionic acid-methyl ester, 1-methyl-phospholene-(3), N-(dimethyl-phosphinylmethyl)-pyrrolidine, isoquinoline, N-vinyl-imidazole, benzyl-triethyl-ammoniumchloride, triphenyl-ethyl-phosphonium-2,4-diaminobenzene-sulfonate, tris-(dimethylamino)-phosphinic oxide, pyridine-N-oxide, dimethyl-aniline, trimethylamine, tetramethylurea, dimethyl formamide, tri-n-butyl-phosphine, benzimidazole, diethylamine, imidazole, benzthiazole, benztriazole, dimethyl-fluorsulfonylethyl-phosphinic oxide, N-cyclohexenyl-(1)-pyrrolidine, 1,2,4-triazole, pentamethylene-imine, butylamine, dimethyl-phosphinous acid-diisopropylamide, triphenyl-phosphine-2-hydroxyethyl-imine, 5,7-dimethyl-2-oxopyrazolo-[1,5-a]pyrimidine, dimethylamino-acetonitrile.

We claim:

1. A process for the preparation of phosphonic acid-dihalides of the formula

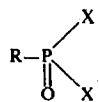

wherein R is alkyl of 1 to 18 carbon atoms, cycloalkyl of 4 to 8 carbon atoms, alkenyl of 2 to 18 carbon atoms, phenyl, phenalkyl or alkyl phenyl both containing a total of 7 to 8 carbon atoms, R may be substituted by chlorine, bromine, a cyano or a lower acyloxy group, and wherein X is halogen, which comprises reacting a phosphonic acid of the formula

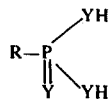

wherein Y is oxygen, or the corresponding acid salt, phosphonic acid monoester and salt thereof, phosphonic acid ester halide, pyrophosphonic acid or pyrophosphonic acid ester with an acid halide of the formula $(CO)_nX_2$ wherein X is chlorine or bromine and n is 1 or 2, in the presence of 0.01 to 0.2% by weight or from 0.2 to 5% by weight of a 1. compound containing at least one tri- to pentavalent nitrogen or phosphorus atom, which in the case of nitrogen is bound with 1 to 4, in the case of phosphorus with at least 3 valences to organic radicals having up to 20 carbon atoms, two of these valences optionally forming a double bond, or 2. mono-, di- or tribasic organic or inorganic fully amidated acid of tri- or pentavalent phosphorus, the N atoms of which optionally being substituted by aliphatic radicals having up to 20 carbon atoms, and the organic radicals of which contain up to 20 carbon atoms, if required, in the presence of an inert solvent.

2. The process as claimed in claim 1, which comprises carrying out the reaction at a temperature in the range of from 65°C to 200°C.

3. The process for the preparation of 2-chloroethane-phosphonic acid-dichloride as claimed in claim 1, which comprises using as starting substance unpurified 2-chloroethane-phosphonic acid-bis-(2-chloroethyl)-ester obtained in the reaction of phosphorus trichloride with ethylene oxide and the subsequent rearrangement of the tris-(2-chloroethyl)-phosphite formed.

* * * * *